United States Patent
Hernández Herrero et al.

(10) Patent No.: US 11,370,742 B2
(45) Date of Patent: Jun. 28, 2022

(54) PROCESS AND INTERMEDIATES FOR THE PREPARATION OF BILASTINE

(71) Applicant: FAES FARMA, S.A., Vizcaya (ES)

(72) Inventors: Gonzalo Hernández Herrero, País Vasco (ES); Neftalí García Domínguez, País Vasco (ES); Pablo Morán Poladura, País Vasco (ES); Tania González García, País Vasco (ES); Álvaro Ganza González, País Vasco (ES); Paloma Tato Cerdeiras, País Vasco (ES)

(73) Assignee: FAES FARMA, S.A.

( * ) Notice: Subject to any disclaimer, the term of this patent is extended or adjusted under 35 U.S.C. 154(b) by 0 days.

(21) Appl. No.: 17/261,731

(22) PCT Filed: Jul. 23, 2019

(86) PCT No.: PCT/EP2019/069772
§ 371 (c)(1),
(2) Date: Jan. 20, 2021

(87) PCT Pub. No.: WO2020/020873
PCT Pub. Date: Jan. 30, 2020

(65) Prior Publication Data
US 2021/0300856 A1    Sep. 30, 2021

(30) Foreign Application Priority Data

Jul. 24, 2018 (EP) .................................... 18382556

(51) Int. Cl.
| | | |
|---|---|---|
| C07C 67/42 | (2006.01) | |
| C07C 45/46 | (2006.01) | |
| C07D 235/04 | (2006.01) | |
| C07D 401/04 | (2006.01) | |
| C07C 51/09 | (2006.01) | |
| C07C 67/00 | (2006.01) | |

(52) U.S. Cl.
CPC .............. *C07C 67/42* (2013.01); *C07C 45/46* (2013.01); *C07C 51/09* (2013.01); *C07C 67/00* (2013.01); *C07D 235/04* (2013.01); *C07D 401/04* (2013.01)

(58) Field of Classification Search
None
See application file for complete search history.

(56) References Cited

U.S. PATENT DOCUMENTS 8,367,704 B2    2/2013 Lee et al.
2009/0104464 A1*  4/2009 Galbo .................... C07C 59/90
562/464

FOREIGN PATENT DOCUMENTS

| CN | 102675101 B | 1/2014 |
| CN | 104151160 A | 11/2014 |
| CN | 104326909 A | 2/2015 |
| WO | 2009/050116 A2 | 4/2009 |
| WO | 2009102155 A2 | 8/2009 |
| WO | 2014188453 A2 | 11/2014 |

OTHER PUBLICATIONS

International Search Report, PCT/EP2019/069772, dated Sep. 20, 2019.
Steven J. Collier et al.," Alternative Synthesis of Bilastine," Synthetic Communications 2011, 41(9), 1394-1402.
Shou-Ri Sheng et al., "A facile conversion of aryl alkyl ketones into methyl e-arylalkanoates using poly[4-(diacetoxyiodo)styrene]," Journal of Chemical Research, 6, 2004, 392-393, DOI:10.3184/0308234041423709.
Bhattacharyya, Jayati, et al.; "Photodecomposition of Acaricide, Fenazaquin, in Aqueous Alcoholic Solution," J. Agric. Food Chern., 2003, vol. 51, pp. 4013-4016.

* cited by examiner

*Primary Examiner* — Amy C Bonaparte
(74) *Attorney, Agent, or Firm* — Tristan A. Fuierer; Casimir Jones, S.C.

(57) ABSTRACT

The invention relates to a process for preparing a compound of (III)

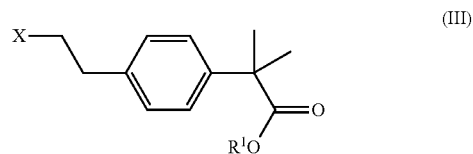

wherein
X is a leaving group; and
$R^1$ is $C_1$-$C_6$ alkyl;
which comprises oxidative rearrangement of a compound of formula (II) or a solvate thereof

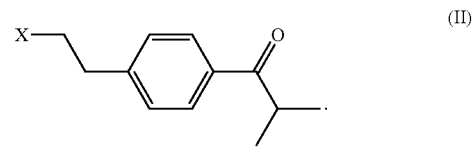

Compounds of formula (III) are key intermediates in the synthesis of Bilastine.

16 Claims, No Drawings

PROCESS AND INTERMEDIATES FOR THE PREPARATION OF BILASTINE

CROSS-REFERENCE TO RELATED APPLICATIONS

This application is filed under the provisions of 35 U.S.C. § 371 and claims the priority of International Patent Application No. PCT/EP2019/069772 filed on 23 Jul. 2019 entitled "PROCESS AND INTERMEDIATES FOR THE PREPARATION OF BILASTINE" in the name of Gonzalo HERNANDEZ HERRERO, et al., which claims priority to European Patent Application No. 18382556.1, filed on 24 Jul. 2018, both of which are hereby incorporated by reference herein in their entirety.

FIELD OF THE INVENTION

The invention relates to a process for the preparation of key intermediates in the synthesis of Bilastine and to new intermediates in said process.

BACKGROUND OF THE INVENTION

Bilastine is a second-generation antihistamine medication which is used in the treatment of allergic rhinoconjunctivitis and urticaria.

Several synthesis of Bilastine has been disclosed in the last years using a compound of formula (III) as key intermediate as it provides a straightforward synthetic route for Bilastine, minimizing protecting group chemistry.

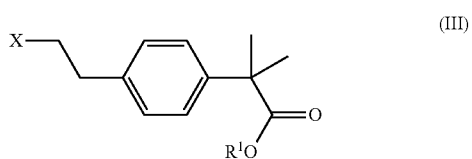

For instance, WO 2009/102155 discloses the preparation of this key intermediate by reacting compound 4 and methyltrimethylsilyl dimethylketene acetal (5) in the presence of a Palladium catalyst, t-Bu$_3$P and ZnF$_2$. This key intermediate is then converted into Bilastine by either reaction with 1-(2-ethoxyethyl)-2-piperidin-4-yl-1H-benzoimidazole (3a) followed by hydrolysis of the ester group or by reaction with 2-(4-piperidinyl)-1H-benzoimidazole (7), followed by alkylation of the benzimidazole nitrogen and hydrolysis of the ester group. However, this cross coupling approach lacks industrial interest due to the instability, availability and cost of the ketene acetal and the phosphine used in the key step of the synthesis.

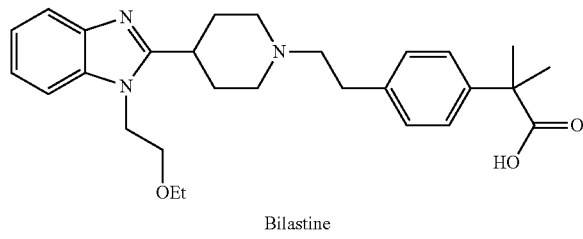

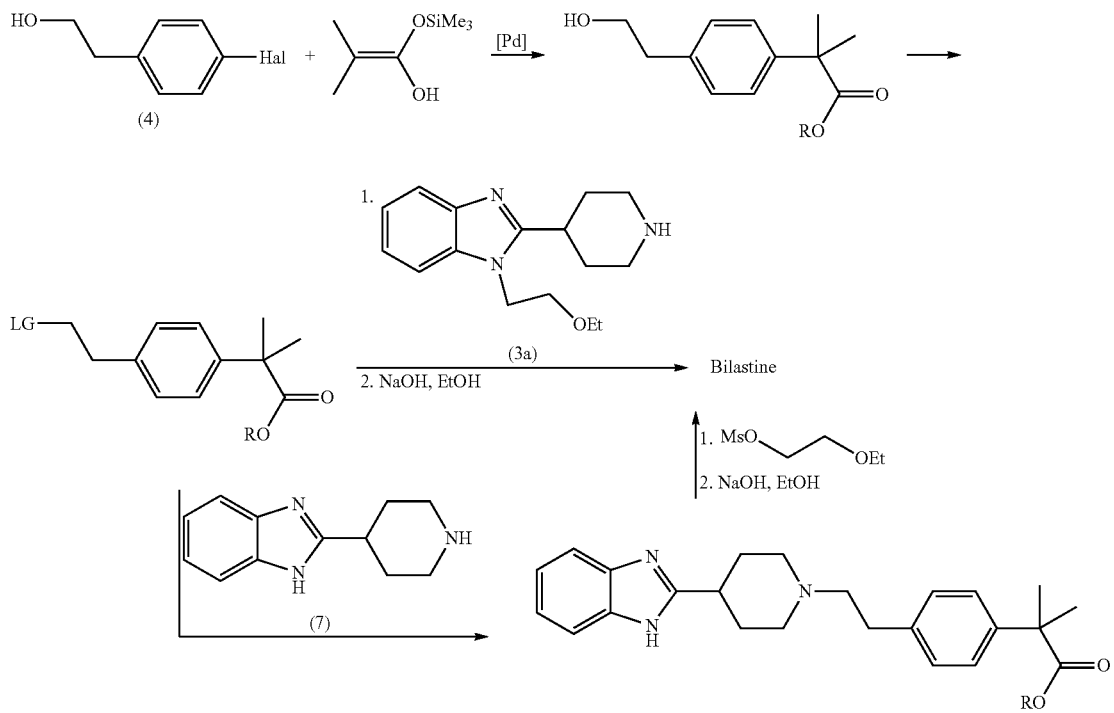

CN 104151160 A refers to the synthesis of compounds similar to key intermediate (III), but which lack a leaving group. The compound is synthesized through the alkylation of the halobenzene compound (2) in the presence of a palladium catalyst and a lithium amide. Then again, this approach uses organometallic reagents and an amide base, which is highly unstable and expensive.

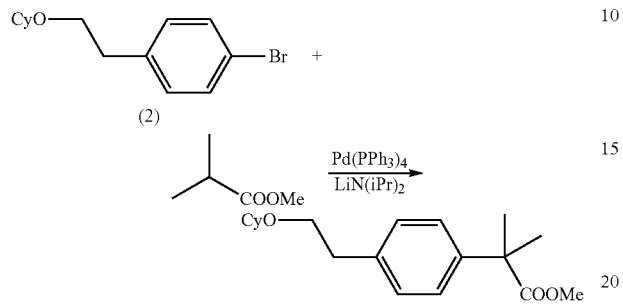

The process for preparing Bilastine disclosed in Synthetic Communications 2011, 41(9), 1394-1402 includes palladium catalyzed vinylation of aryl bromide (3) with vinyl tributylstannane or with vinylboronic anhydride followed by hydroboration of the resulting styrene (11). This alternative cross coupling approach uses in the first step high cost and low available vinyl synthons (and highly toxic in the case of the tin compound). Besides, the anti-Markovnikov hydroxylation step is performed using the well-known and undesirable borane (highly toxic and flammable gas), which also undermines its industrial applicability.

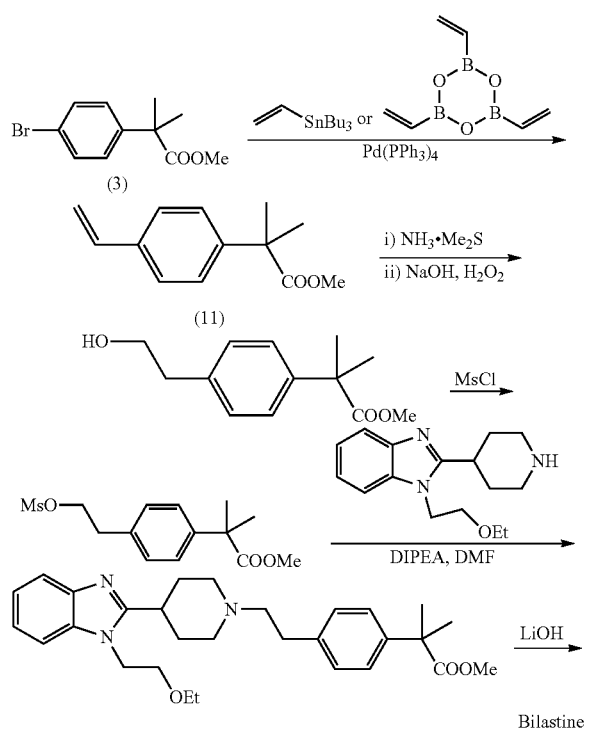

CN 104326909 A and CN 102675101 A refer to a process for the synthesis of key intermediate (III) which comprises acylation of 2-methyl-2-phenyl-propanoic acid or an ester thereof in the presence of a Lewis acid and subsequent reduction of the oxo group. This approach, even if industrially applicable, uses stoichiometric reagents both in the acylation and the reduction step and involves the generation of high amounts of residues.

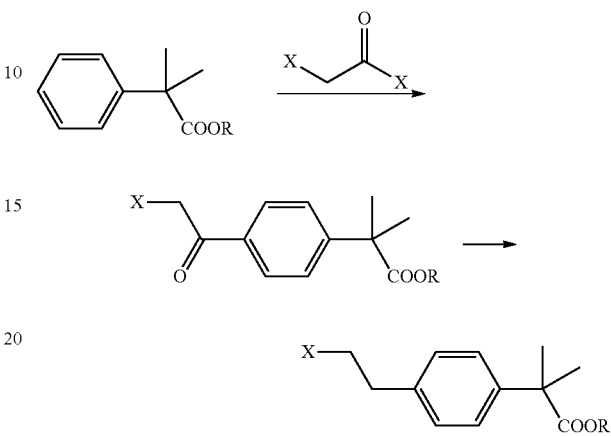

In general, the methods disclosed in the prior art for the preparation of compounds of formula (III) according to the present invention, require the use of organometallic reagents, toxic reagents, harsh reaction conditions or have a low productivity and, therefore, are not suitable for industrial production.

It is therefore necessary to develop a new process for obtaining compounds of formula (III), which are key intermediates in the synthesis of Bilastine, which overcome all or part of the problems associated with the known processes belonging to the state of the art.

SUMMARY OF THE INVENTION

The invention faces the problem of providing a new process for the preparation of formula (III) and to intermediates thereof.

In contrast to processes of the prior art, the process of the invention meets the needs of industrial production. It allows preparing compounds of formula (III) in the absence of organometallic and toxic reagents, in short reaction times, is a simple and low cost process and gives rise to the desired product with a very high productivity.

The inventors have found that compounds of formula (III) can be obtained in a very straightforward manner by acylation and subsequent oxidative rearrangement of readily available and economical starting materials. As shown in the experimental section, this process not only avoids the use of highly toxic, unstable and/or expensive reagents, but also leads to the compounds of formula (III) in shorter reaction times and with higher productivity than prior art processes. All these features make the process of the invention very cost-efficient and therefore highly suitable for industrial scale production.

The compounds of formula (III) obtained by the process of the invention already include the leaving group required for subsequent reaction with the piperidinyl compound and so does not require additional reaction steps for its use in the preparation of Bilastine.

Thus, in a first aspect the invention is directed to a process for preparing a compound of formula (III)

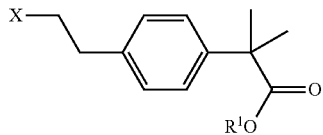
(III)

or a solvate thereof wherein
X is a leaving group; and
$R^1$ is $C_1$-$C_6$ alkyl;
which comprises oxidative rearrangement of a compound of formula (II) or a solvate thereof

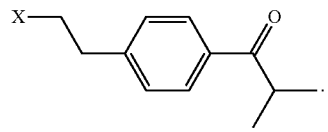
(II)

In a second aspect the invention is directed to the use of a compound of formula (II)

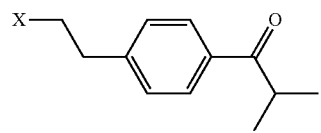
(III)

or a solvate thereof wherein X is a leaving group as an intermediate in the preparation of Bilastine.

In a third aspect, the invention is directed to a compound of formula (II')

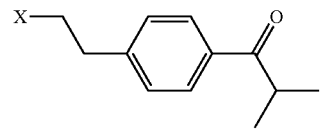
(II')

or a solvate thereof wherein X is selected from Cl, I, OMs, OTs and OTf.

DETAILED DESCRIPTION OF THE INVENTION

The term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, n-propyl, i-propyl, n-butyl, i-butyl, t-butyl, pentyl, hexyl. Preferably, it is methyl.

The term "aryl" refers to an aromatic group having between 6 and 10 ("$C_6$-$C_{10}$ aryl"), preferably 6 or 10 carbon atoms, comprising 1 or 2 aromatic nuclei fused to one another. Illustrative examples of aryl groups include phenyl, naphthyl, indenyl, phenanthryl, etc. Preferably, it is phenyl.

The term "($C_6$-$C_{10}$)aryl($C_1$-$C_6$)alkyl" refers to an alkyl group as defined above substituted with an aryl group as defined above. Examples of such groups include benzyl, phenylethyl, phenylpropyl, naphthylmethyl, etc. Preferably, it is benzyl.

The term "haloalkyl" refers to an alkyl group as defined above containing from 1 to 6 ("$C_1$-$C_6$ haloalkyl"), preferably from 1 to 3 ("$C_1$-$C_3$ haloalkyl"), carbon atoms wherein at least one hydrogen atom has been replaced by halogen. Examples of haloalkyl groups include but are not limited to $CF_3$, $CCl_3$, $CHF_2$, $CF_2CF_3$. Preferably, it is —$CF_3$.

The term "halogen" refers to bromine, chlorine, iodine or fluorine.

The term "leaving group" refers to a functional group or an atom that can be displaced by another functional group in a substitution reaction, such as a nucleophilic substitution reaction. Suitable leaving groups are well known in the art. In a particular embodiment, the leaving group is selected from halogen, $C_1$-$C_6$ alkylsulfonates, $C_1$-$C_6$ haloalkylsulfonates and ($C_1$-$C_6$)alkyl($C_6$-$C_{10}$)arylsulfonates, such as chloro, bromo, iodo, mesylate (OMs), triflate (OTf), tosylate (OTs) and the like.

The invention also refers to "salts" of the compounds described in the present description. By way of illustration, said salts can be acid addition salts, base addition salts or metal salts, and can be synthesized from the parent compounds containing a basic or acid moiety by means of conventional chemical processes known in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of said acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, trifluoroacetate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts. In a particular embodiment, the salt is an acid addition salt, such as hydrochloride, hydrobromide, hydroiodide, sulfate, nitrate, phosphate, acetate, maleate, fumarate, citrate, oxalate, succinate, tartrate, malate, mandelate, methanesulfonate, p-toluenesulfonate, trifluoroacetate or camphorsulfonate. Preferably, it is selected from HCl, HBr, $H_3PO_4$, $H_2SO_4$, MsOH, pTsOH, TFA, citrate and fumarate salt.

Likewise, the compounds described in the present description can be obtained or used both as free compounds or as solvates (e.g., hydrates, alcoholates, etc.), both forms being included within the scope of the present invention. The solvation methods are generally known in the state of the art. Preferably, the solvate is a hydrate.

The term "organic solvent" includes for example cyclic and acyclic ethers (e.g. $Et_2O$, $iPr_2O$, $tBu_2O$, MeOtBu, 1,4-dioxane, tetrahydrofuran, methyltetrahydrofuran), hydrocarbon solvents (e.g. pentane, hexane, heptane), halogenated solvents (e.g. dichloromethane, chloroform, chlorobenzene), aromatic solvents (e.g. toluene, xylene), ketones (e.g.

acetone, butanone, pentanone, methyl ethyl ketone, ethyl isopropyl ketone), esters (e.g. EtOAc, iPrOAc), nitriles (e.g. acetonitrile, benzonitrile), amides (e.g. DMF, DMA, HMPA, NMP), alcohols (e.g. methanol, ethanol, propanol, isopropanol, sec-butanol, t-butanol), sulfoxides (DMSO) and mixtures thereof.

In a first aspect, the invention is directed to a process for preparing a compound of formula (III)

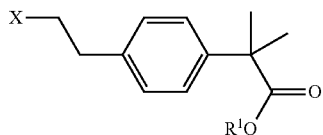

or a solvate thereof wherein
X is a leaving group; and
$R^1$ is $C_1$-$C_6$ alkyl;
which comprises oxidative rearrangement of a compound of formula (II) or a solvate thereof

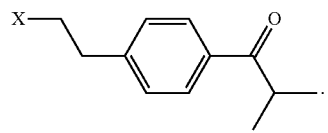

In an embodiment, X is selected from Cl, Br, I, OMs, OTs and OTf. Preferably, X is selected from Cl, Br and I; more preferably from Cl and Br; even more preferably X is Cl.

In another preferred embodiment, $R^1$ is $C_1$-$C_3$ alkyl; preferably Me or Et; even more preferably $R^1$ is Me.

In a particular embodiment, the process of the invention comprises:
(a) acylation of a compound of formula (I)

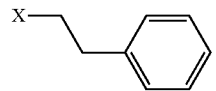

or a solvate thereof wherein X is a leaving group, to provide a compound of formula (II)

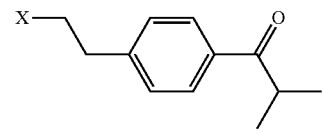

or a solvate thereof, and
(b) oxidative rearrangement of a compound of formula (II), or a solvate thereof, to provide a compound of formula (III)

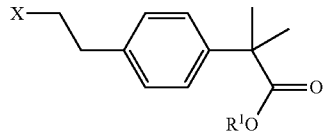

or a solvate thereof wherein $R^1$ is $C_1$-$C_6$ alkyl.

In an embodiment, X is selected from Cl, Br and I and $R^1$ is $C_1$-$C_3$ alkyl.

Though compounds of formula (II) contain a leaving group in beta-position to the aromatic ring, the inventors have found that oxidative rearrangement of these compounds proceeds very efficiently (e.g. Olah et al., J. Am. Chem. Soc. 1982, 104, 5168-5172, reports the instability of this type of compounds under acidic conditions). Consequently, this process allows preparing compounds of formula (III) in a very straightforward manner.

Additionally, the inventors have found that the process of the invention leads to compounds of formula (III) in high yield and short reaction times. It does not require the use of organometallic or toxic reagents, is simple and low cost and gives rise to the desired product with a very high productivity. Consequently, this process is very suitable for industrial scale production.

In a particular embodiment, the process of the invention further comprises converting the compound of formula (III), or a solvate thereof, into Bilastine, or a salt or solvate thereof.

Compounds of formula (III) can be converted into Bilastine through processes known from the prior art (e.g. WO 2009/102155, CN 104326909 A, CN 102675101 A, Synthetic Communications 2011, 41(9), 1394-1402).

In a particular embodiment, converting the compound of formula (III), or a solvate thereof, into Bilastine, or a salt or solvate thereof, comprises:
(c) reacting a compound of formula (III)

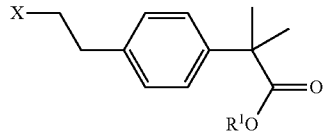

or a solvate thereof wherein X and $R^1$ are as defined above,
with a compound of formula (IV)

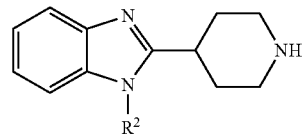

or a salt or solvate thereof wherein $R^2$ is selected from H and —$CH_2CH_2OEt$;

to provide a compound of formula (V)

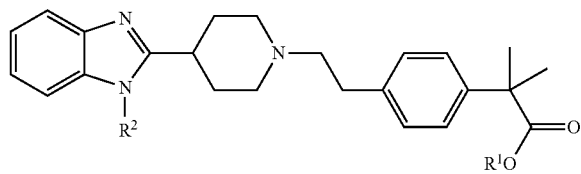

or a salt or solvate thereof; and
(d) converting the compound of formula (V), or a salt or solvate thereof, into Bilastine, or a salt or solvate thereof.

When $R^2$ in the compound of formula (IV), or a salt or solvate thereof, is $CH_2CH_2OEt$, a compound of formula (V) wherein $R^2$ is $CH_2CH_2OEt$ is obtained after step (c). In this case, step (d) comprises hydrolysis of the ester group in the compound of formula (V) wherein $R^2$ is $CH_2CH_2OEt$, or a salt or solvate thereof, to provide Bilastine, or a salt or solvate thereof.

When $R^2$ in the compound of formula (IV), or a salt or solvate thereof, is H, a compound of formula (V) wherein $R^2$ is H is obtained after step (c). In this case, step (d) comprises:
(d1) reacting a compound of formula (V), or a salt or solvate thereof, wherein $R^2$ is H, with a compound of formula (VI)

wherein Y is a leaving group,
to provide a compound of formula (V), or a salt or solvate thereof, wherein $R^2$ is —$CH_2CH_2OEt$; and
(d2) hydrolysis of the ester group in the compound of formula (V), or a salt or solvate thereof, wherein $R^2$ is —$CH_2CH_2OEt$ to provide Bilastine or a salt or solvate thereof.

In an embodiment, Y is selected from Cl, Br, I, OMs, OTs and OTf.

The inventors have surprisingly found that reaction of the compound of formula (V), or a salt or solvate thereof, wherein $R^2$ is H, with a compound of formula (VI) as defined above, can be carried out under reaction conditions that also hydrolyze the ester group, thus directly giving rise to Bilastine, or a salt or solvate thereof, from the compound of formula (V), or a salt or solvate thereof, wherein $R^2$ is H.

In this way, when the hydrolysis of the ester group in the compound of formula (V), or a salt or solvate thereof, takes place under the reaction conditions used for step (d1), Bilastine is obtained in a very straightforward manner: just 4 synthetic steps from the starting compound of formula (I).

Surprisingly, said process proceeds in a very efficient way, leading directly to Bilastine in a high yield and purity and avoiding the need of an additional hydrolysis step, in contrast to other processes in the prior art.

In a particular embodiment, steps (d1) and (d2) are carried out in a one pot process. That is, both steps are carried out in the same reaction vessel or the same reactor without the isolation of the intermediate of formula (V) wherein $R^2$ is —$CH_2CH_2OEt$. This avoids the need of lengthy separation process and purification of the intermediate. Consequently, said one-pot process shortens the number of reaction steps required overall to obtain Bilastine, and saves time and resources.

In a further embodiment, hydrolysis of the ester group in the compound of formula (V), or a salt or solvate thereof, takes place under the reaction conditions used for step (d1). In this case, Bilastine, or a salt or solvate thereof, is directly obtained from a compound of formula (V), or a salt or solvate thereof, wherein $R^2$ is H.

Therefore, in a further embodiment of the invention, step (d) comprises reacting a compound of formula (V), or a salt or solvate thereof, wherein $R^2$ is H with a compound of formula (VI)

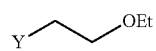

wherein Y is a leaving group,
and hydrolysis of the ester group in a compound of formula (V), or a salt or solvate thereof, to provide Bilastine or a salt or solvate thereof.

In this case, both reaction with the compound of formula (VI) and hydrolysis of the ester group take place in a single reaction step.

In another embodiment, the compound obtained after step (d1) is isolated, and optionally purified, before performing step (d2).

According to another embodiment of the invention, converting the compound of formula (III), or a solvate thereof, into Bilastine, or a salt or solvate thereof, comprises:
(c') hydrolysis of a compound of formula (III)

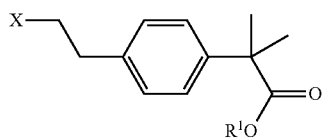

or a solvate thereof wherein X and $R^1$ are as defined above,
to provide a compound of formula (III')

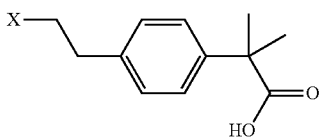

or a salt or solvate thereof;
(d') reacting a compound of formula (III'), or a salt or solvate thereof, with a compound of formula (IV)

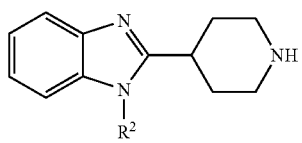

or a salt or solvate thereof wherein $R^2$ is selected from H and —$CH_2CH_2OEt$;

to provide a compound of formula (V')

(V')

or a salt or solvate thereof; and
(e') if needed, converting the compound of formula (V'), or a salt or solvate thereof, into Bilastine, or a salt or solvate thereof.

Step (e') is needed if $R^2$ in the compound of formula (IV) is H.

Otherwise, when $R^2$ in the compound of formula (IV) is —$CH_2CH_2OEt$, Bilastine is obtained after step (d'). In this case, the above mentioned process to convert the compound of formula (III) into Bilastine only comprises steps (c') and (d').

When $R^2$ in the compound of formula (IV), or a salt or solvate thereof, is H, a compound of formula (V') wherein $R^2$ is H is obtained after step (d'). In this case, step (e') comprises reacting a compound of formula (V'), or a salt or solvate thereof, wherein $R^2$ is H, with a compound of formula (VI)

(VI)

wherein Y is a leaving group, to provide Bilastine or a salt or solvate thereof.

In an embodiment, Y is selected from Cl, Br, I, OMs, OTs and OTf.

Preferably, the processes for preparing Bilastine according to the invention, comprise the above disclosed steps (steps (a) to (d) or steps (a) to (e')) in a sequential order without further reaction steps (e.g. protection or deprotection of functional groups). That is, in a preferred embodiment, the processes for preparing Bilastine according to the invention, consist of the above disclosed reaction steps (steps (a) to (d) or steps (a) to (e')). Unless otherwise specified, the process can include isolation and purification steps after some or all of these reaction steps.

Oxidative Rearrangement of a Compound of Formula (II)

In an embodiment, oxidative rearrangement of a compound of formula (II), or a solvate thereof, to provide a compound of formula (III), or a solvate thereof, is carried out in the presence of an oxidizing agent and a tri($C_1$-$C_6$) alkyl orthoester, or a ($C_1$-$C_6$)alkanol or a mixture thereof.

In an embodiment, the tri($C_1$-$C_6$)alkyl orthoester is selected from trimethyl and triethyl orthoester.

In a particular embodiment, the triethyl-trimethylorthoester is selected from triethyl-trimethylorthoformate.

In an embodiment, the ($C_1$-$C_6$)alkanol is selected from MeOH and EtOH.

Preferably, the tri($C_1$-$C_6$)alkyl orthoester, ($C_1$-$C_6$)alkanol or the mixture thereof is used as solvent of the reaction.

Suitable oxidizing agents include iodine oxidizing agents, such as $I_2$, ICl, $ICl_3$, $HIO_3$, $PhI(OAc)_2$, $PhI(OCOCF_3)_2$, $PhI(OTf)_2$, PhI(OH)OTs, PhIO, NIS, IBX, DMP. In an embodiment, the oxidizing agent is selected from $I_2$, ICl, $HIO_3$ and $PhI(OAc)_2$.

In a particular embodiment, the oxidizing agent is present in an amount of from 1.0 to 10.0 molar equivalents with respect to the compound of formula (II); preferably from 1.0 to 5.0, more preferably from 1.0 to 3.0 molar equivalents.

In a preferred embodiment, the reaction is carried out in the presence of an acid. Suitable acids that can be used as catalyst include inorganic acids and organic acids such as, for example, sulfuric acid, hydrochloric acid, hydrobromic acid, nitric acid, phosphoric acid, acetic acid, trifluoroacetic acid, camphorsulfonic acid, p-toluenesulfonic acid, methanesulfonic acid, maleic acid, fumaric acid, citric acid, oxalic acid, succinic acid, tartaric acid and malic acid. In a particular embodiment, the acid is selected from HCl, HBr, $H_3PO_4$, $H_2SO_4$, MsOH, pTsOH and TFA. Preferably, it is $H_2SO_4$ or HCl.

Preferably, the acid catalyst is generated in situ from an acid precursor. Therefore, in a preferred embodiment, the reaction is carried out in the presence of an acid precursor. Suitable acid precursors are known by the skilled person and include alkylacid chloride or alkyl chloroformate, such as, for example, 2,2-dimethyl propionyl chloride, acetyl chloride, propionyl chloride, ethyl chloroformate, methyl chloroformate, propyl chloroformate, benzyl chloroformate, trichloromethyl chloroformate. In an embodiment, the reaction is carried out in the presence of a hydrochloric acid precursor, such as 2,2-dimethyl propionyl chloride or ethyl chloroformate.

In a particular embodiment, the acid is present in an amount of from 0.01 to 0.9 molar equivalents with respect to the compound of formula (II); preferably from 0.05 to 0.6, more preferably from 0.1 to 0.5 molar equivalents.

In an embodiment, the reaction is performed at a temperature between −20° C. and 150° C., preferably at a temperature between 20° C. and 130° C., preferably between 20° C. and 100° C.

In an embodiment of the invention, the oxidative rearrangement is carried out in the presence of a tri($C_1$-$C_6$)alkyl orthoester, a ($C_1$-$C_6$)alkanol or a mixture thereof, an oxidizing agent and an acid catalyst.

In a particular embodiment, the oxidative rearrangement is carried out in the presence of a tri($C_1$-$C_6$)alkyl orthoester, an iodine oxidizing agent and an acid catalyst.

In a particular embodiment, the reaction is carried out in the absence of a solvent (other than the reagents used for the reaction). Preferably, the tri($C_1$-$C_6$)alkyl orthoester is used as solvent of the reaction.

In another embodiment, the oxidative rearrangement is carried out in the presence of an organic solvent. In an embodiment, the organic solvent is selected from cyclic and acyclic ethers (e.g. $Et_2O$, $iPr_2O$, $tBu_2O$, MeOtBu, 1,4-dioxane, THF, 2-methyl-THF), hydrocarbon solvents (e.g. pentane, hexane, heptane), halogenated solvents (e.g. dichloromethane, chloroform, chlorobenzene), aromatic solvents (e.g. toluene, xylene), alcohols (e.g. methanol, ethanol, propanol, isopropanol, sec-butanol, t-butanol) and mixtures thereof. Preferably, the organic solvent is an alcohol; more preferably a $C_{1-6}$ alkanol, such as methanol, ethanol, propanol, isopropanol, sec-butanol, t-butanol; even more preferably it is methanol.

In an embodiment, the oxidative rearrangement is carried out in the presence of trimethyl orthoformate (TMOF), an iodine oxidizing agent and an acid catalyst.

In another embodiment, the oxidative rearrangement is carried out in the presence of trimethyl orthoformate (TMOF), an iodine oxidizing agent, an acid catalyst and an organic solvent.

In another embodiment, the oxidative rearrangement is carried out in the presence of trimethyl orthoformate (TMOF), an iodine oxidizing agent selected from $I_2$, ICl, $HIO_3$ and $PhI(OAc)_2$, and an acid selected from HCl, HBr, $H_3PO_4$, $H_2SO_4$, MsOH, pTsOH and TFA.

In a further embodiment, the oxidative rearrangement is carried out in the presence of trimethyl orthoformate (TMOF), an iodine oxidizing agent selected from $I_2$, ICl, $HIO_3$ and $PhI(OAc)_2$, an acid selected from HCl, HBr, $H_3PO_4$, $H_2SO_4$, MsOH, pTsOH and TFA, and an organic solvent.

In a further embodiment, the oxidative rearrangement is carried out in the presence of trimethyl orthoformate (TMOF), an iodine oxidizing agent selected from $I_2$, ICl, $HIO_3$ and $PhI(OAc)_2$, an acid selected from $H_2SO_4$ and HCl.

In another embodiment, the oxidative rearrangement is carried out in the presence of trimethyl orthoformate (TMOF), an iodine oxidizing agent selected from $I_2$, ICl, $HIO_3$ and $PhI(OAc)_2$, an acid selected from $H_2SO_4$ and HCl, and an organic solvent.

Acylation of a Compound of Formula (I)

Acylation of a compound of formula (I), or a solvate thereof, is carried out in the presence of a suitable acylating agent. In an embodiment, the acylating agent is selected from $(iPrCO)_2O$ and a compound of formula iPrCO—Z, wherein Z is selected from OH, Cl, Br and I. Preferably, the acylating agent is iPrCO—Cl.

In a particular embodiment, the acylating agent is present in an amount of from 1.0 to 10.0 molar equivalents with respect to the compound of formula (I); preferably from 1.0 to 5.0, more preferably from 1.0 to 3.0 molar equivalents.

In an embodiment, the reaction is carried out in the presence of a protic acid and/or a Lewis acid. Suitable protic and Lewis acid for the Friedel Crafts acylation are known in the prior art. In an embodiment, the acid is selected from $AlCl_3$, $AlBr_3$, $FeCl_3$, $FeBr_3$, $BF_3$, $BBr_3$, $BCl_3$, ZnO, $ZnCl_2$, $ZnBr_2$, $TiCl_4$, $SnCl_4$, $SiCl_4$, $POCl_3$, $FeSO_4$ and hydrates or solvate thereof, HCl, $H_2SO_4$, $H_3PO_4$, $HClO_4$, $HBF_4$, $ClSO_3H$, MsOH and TfOH. Preferably, the acid is $AlCl_3$.

In a particular embodiment, the acid is present in an amount of from 0.1 to 10.0 molar equivalents with respect to the compound of formula (I); preferably from 0.1 to 5.0, more preferably from 0.5 to 3.0 molar equivalents.

In a particular embodiment, the acylation reaction is carried out in the presence of an organic solvent. Suitable solvents include, for example, ethers, hydrocarbon solvents, halogenated solvents, aromatic solvents, ketones, esters, and mixtures thereof. In an embodiment, the solvent is a hydrocarbon solvent, such as pentane, hexane or heptane. In an embodiment, the reaction is carried out in the presence of a non-polar organic solvent, such as an ether (e.g. $Et_2O$, $iPr_2O$, $tBu_2O$, MeOtBu, 1,4-dioxane), a hydrocarbon solvent (e.g. pentane, hexane, heptane) a halogenated solvent (e.g. dichloromethane, chloroform) or an aromatic solvent (e.g. toluene, xylene).

In another preferred embodiment, the reaction is carried out neat, that is, in the absence of a solvent.

Preferably, the reaction is carried out neat or in the presence of a non-polar organic solvent.

In an embodiment, the reaction is performed at a temperature between −78° C. and 100° C., preferably at a temperature between −20° C. and 60° C., preferably between 0° C. and 40° C.

In a particular embodiment, the acylation reaction is carried out in the presence of a suitable acylating agent and an acid.

In another embodiment, the acylation reaction is carried out in the presence of an acylating agent is selected from $(iPrCO)_2O$ and a compound of formula iPrCO—Z, wherein Z is selected from OH, Cl, Br and I, and a protic acid and/or a Lewis acid.

In a preferred embodiment, the acylation reaction is carried out in the presence of iPrCO—Cl and $AlCl_3$.

Reaction of a Compound of Formula (III) or (III') with a Compound of Formula (IV)

Reaction of a compound of formula (III) or (III') with a compound of formula (IV) to provide a compound of formula (V) or (V'), respectively, can be carried out as disclosed previously in the prior art.

In a particular embodiment of the invention, the reaction is carried out in the presence of a base and an organic solvent.

Suitable bases include inorganic and organic bases, such as an alkali metal carbonate or bicarbonate (e.g. $Na_2CO_3$, $K_2CO_3$, $Cs_2CO_3$, $Li_2CO_3$, $NaHCO_3$, $KHCO_3$, $CsHCO_3$, $LiHCO_3$), an alkali metal phosphate (e.g. $Na_3PO_4$, $K_3PO_4$, $Na_2HPO_4$, $K_2HPO_4$, $NaH_2PO_4$, $KH_2PO_4$), an alkali metal alkoxide (e.g. NaOMe, KOMe, NaOEt, KOEt, NaOtBu, KOtBu), an alkali metal hydroxide (e.g. NaOH, KOH, LiOH, CsOH), an aliphatic or aromatic amine (e.g. $Me_2NH$, $Et_2NH$, $iPr_2NH$, $Bu_2NH$, $Me_3N$, $Et_3N$, $Bu_3N$, $iPr_2EtN$, N-methylmorpholine, pyridine, DMAP, aniline, N,N-dimethylaniline). Preferably, the base is an inorganic base, more preferably it is an alkali metal carbonate, bicarbonate or phosphate.

In an embodiment, the organic solvent is a polar organic solvent, such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), alcohol (e.g. methanol, ethanol, propanol, isopropanol, sec-butanol, t-butanol), or mixtures thereof. In a further embodiment, the organic solvent is a polar aprotic organic solvent, such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), or mixtures thereof.

In a preferred embodiment, the reaction is carried out in the presence of an inorganic base and a polar aprotic organic solvent.

In an embodiment, the reaction is performed at a temperature between 20° C. and 180° C., preferably at a temperature between 20° C. and 160° C., preferably between 50° C. and 150° C.

Reaction of a Compound of Formula (V) or (V') Wherein $R^2$ is H with a Compound of Formula (VI)

Reaction of a compound of formula (V) or (V') wherein $R^2$ is H with a compound of formula (VI) to provide a compound of formula (V) wherein $R^2$ is —$CH_2CH_2OEt$ or Bilastine, respectively, can be carried out as disclosed previously in the prior art.

In a particular embodiment of the invention, the reaction is carried out in the presence of a base and an organic solvent.

Suitable bases include inorganic and organic bases, such as an alkali metal carbonate or bicarbonate (e.g. $Na_2CO_3$, $K_2CO_3$, $Cs_2CO_3$, $Li_2CO_3$, $NaHCO_3$, $KHCO_3$, $CsHCO_3$, $LiHCO_3$), an alkali metal phosphate (e.g. $Na_3PO_4$, $K_3PO_4$, $Na_2HPO_4$, $K_2HPO_4$, $NaH_2PO_4$, $KH_2PO_4$), an alkali metal alkoxide (e.g. NaOMe, KOMe, NaOEt, KOEt, NaOtBu, KOtBu), an alkali metal hydroxide (e.g. NaOH, KOH, LiOH, CsOH), an aliphatic or aromatic amine (e.g. Me₂NH, Et₂NH, iPr₂NH, Bu₂NH, Me₃N, Et₃N, Bu₃N, iPr₂EtN, N-methylmorpholine, pyridine, DMAP, aniline, N,N-dimethylaniline). Preferably, the base is an inorganic base; more preferably an alkali metal hydroxide or alkoxide; even more preferably an alkali metal hydroxide such as NaOH, KOH, LiOH or CsOH.

In an embodiment, the organic solvent is a polar organic solvent, such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), alcohol (e.g. methanol, ethanol, propanol, isopropanol, sec-butanol, t-butanol), or mixtures thereof. In a further embodiment, the organic solvent is a polar aprotic organic solvent, such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), or mixtures thereof.

In a preferred embodiment, the reaction is carried out in the presence of an inorganic base, preferably an alkali metal hydroxide, and a polar organic solvent.

In an embodiment, the reaction is performed at a temperature between 0° C. and 180° C., preferably at a temperature between 20° C. and 160° C., preferably between 30° C. and 100° C.

In a preferred embodiment of the invention, hydrolysis of the ester group to the carboxylic acid takes place under the reaction conditions for reacting the compound of formula (V) wherein $R^2$ is H with a compound of formula (VI). In this case, Bilastine or a salt or solvate thereof is directly obtained without the need of an additional reaction step. In a particular embodiment, this is carried out in the presence of an inorganic base, preferably an alkali metal hydroxide (e.g. KOH or NaOH), and a polar organic solvent (e.g. DMSO).

Hydrolysis of the Ester Group

Hydrolysis of the ester group in a compound of formula (V) wherein $R^2$ is —CH₂CH₂OEt or in a compound of formula (III) to provide Bilastine or a compound of formula (III'), respectively, can be carried out as disclosed previously in the prior art.

In an embodiment, the reaction is carried out by acid or basic hydrolysis. In a particular embodiment, hydrolysis is carried out by treatment with an acid or a base under heat. Suitable acids include acetic acid, trifluoroacetic acid, methanesulfonic acid, trifluoromethanesulfonic acid, HCl, HBr, HF, HClO₄, H₂SO₄, HNO₃, H₃PO₄, formic acid, propionic acid, butyric acid, malic acid, citric acid, benzoic acid, p-toluenesulfonic acid, oxalic acid and succinic acid, preferably HCl, HBr and H₂SO₄. Suitable bases include alkali metal carbonates or bicarbonates (e.g. Na₂CO₃, K₂CO₃, Cs₂CO₃, Li₂CO₃, NaHCO₃, KHCO₃, CsHCO₃, LiHCO₃), alkali metal phosphates (e.g. Na₃PO₄, K₃PO₄, Na₂HPO₄, K₂HPO₄, NaH₂PO₄, KH₂PO₄), alkali metal alkoxides (e.g. NaOMe, KOMe, NaOEt, KOEt, NaOtBu, KOtBu), and alkali metal hydroxides (e.g. NaOH, KOH, LiOH, CsOH). Preferably, the base is an alkali metal hydroxide or alkoxide; more preferably an alkali metal hydroxide such as NaOH, KOH, LiOH or CsOH.

In an embodiment, the reaction is carried out in the presence of water, an organic solvent, or mixtures thereof.

In a particular embodiment, the reaction is carried out in the presence of an organic solvent, preferably a polar organic solvent such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), alcohol (e.g. methanol, ethanol, propanol, isopropanol, sec-butanol, t-butanol), or mixtures thereof.

In a preferred embodiment, the reaction is carried out in the presence of an inorganic base, preferably an alkali metal hydroxide, and a polar organic solvent. In an embodiment, the reaction is performed at a temperature between 0° C. and 180° C., preferably at a temperature between 20° C. and 160° C., preferably between 30° C. and 100° C.

In a preferred embodiment, hydrolysis of the ester group takes place under the basic conditions used of the reaction of the compound of formula (V) wherein $R^2$ is H with a compound of formula (VI), so that Bilastine, or a salt or solvate thereof, is directly obtained in a single reaction step from the compound of formula (V) wherein $R^2$ is H, or a salt or solvate thereof.

In another aspect, the invention is directed to the use of a compound of formula (II)

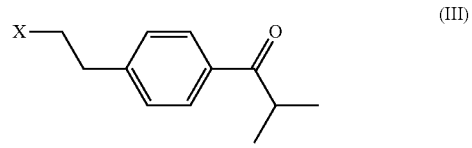

(III)

or a solvate thereof wherein X is a leaving group as an intermediate in the preparation of Bilastine.

In an embodiment, X is selected from Cl, Br, I, OMs, OTs and OTf; preferably X is Cl or Br; more preferably X is Cl.

In a further aspect, the invention is directed to a compound of formula (II')

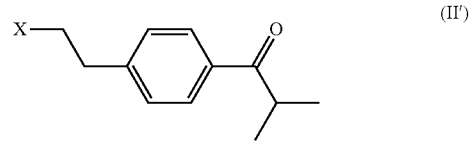

(II')

or a solvate thereof wherein X is selected from Cl, I, OMs, OTs and OTf.

In a preferred embodiment, X is Cl.

It should be understood that the scope of the present disclosure includes all the possible combinations of embodiments disclosed herein.

EXAMPLES

Example 1: Preparation of 1-(4-(2-chloroethyl)phenyl)-2-methylpropan-1-one

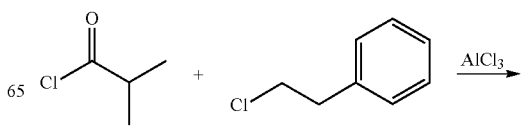

-continued

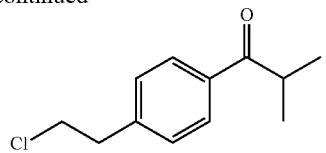

In a reaction vessel iPrCOCl (8.2 g) was cooled to 9° C. and mixed with AlCl$_3$ (5.2 g). 2-Chloroethylbenzene (4.3 g) was added dropwise and the mixture was stirred for 60 minutes, poured over HCl 1M (50 mL) at 0° C. TBME (10 mL) was added and the mixture was stirred. The organic layer was washed with NaOH 1M (25 mL), separated, dehydrated with anhydrous sodium sulfate and then condensed and the solvent was removed under vacuum. 7.4 g of 1-(4-(2-chloroethyl)phenyl)-2-methylpropan-1-one were obtained in a 100% yield and a 90% purity.

Example 2: Preparation of 2-[4-(2-Chloro-ethyl)-phenyl]-2-methyl-propionic Acid Methyl Ester

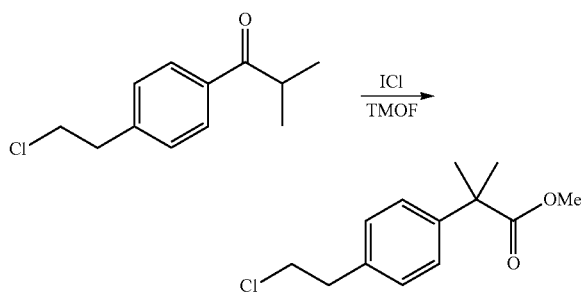

In a round-bottom flask with a reflux condenser, ICl (9.6 mL) was added to a solution of 1-[4-(2-chloro-ethyl)-phenyl]-2-methyl-propan-1-one (13.42 g) in TMOF (55 mL). The mixture reacted fairly vigorously in an exothermic reaction. After few minutes, when the bubbling and the reflux had stopped, the mixture was cooled down and the workup was performed as follows: it was quenched with a saturated solution of sodium bicarbonate (120 mL) and extracted with dichloromethane (80 mL×3). The organic layer was washed with a solution of Na$_2$S$_2$O$_3$ (10%, 150 mL), dried with anhydrous sodium sulfate and concentrated. 15.03 g of 2-[4-(2-chloro-ethyl)-phenyl]-2-methyl-propionic acid methyl ester were obtained in a 98% yield and 85% purity.

Example 3: Preparation of 2-[4-(2-Chloro-ethyl)-phenyl]-2-methyl-propionic Acid Methyl Ester

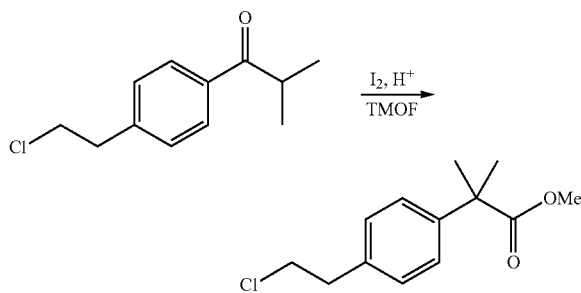

I$_2$ (794 mg) was added to a round-bottom flask with 1-[4-(2-chloro-ethyl)-phenyl]-2-methyl-propan-1-one (200 mg) in TMOF (913 μL). The mixture was stirred for five minutes before sulphuric acid (22 μL) was added. At this point, the vessel was heated at 80° C. After 1 hour, workup was accomplished by the addition of a solution of NaHCO$_3$ (5 mL) and then extraction with dichloromethane (5 mL×3). The organic layer was washed with a solution of Na$_2$S$_2$O$_3$ (20 mL), dried with anhydrous sodium sulfate and concentrated under vacuum. 0.226 g of 2-[4-(2-Chloro-ethyl)-phenyl]-2-methyl-propionic acid methyl ester were obtained in a 99% yield and 86% purity.

Example 4: Preparation of 2-[4-(2-Chloro-ethyl)-phenyl]-2-methyl-propionic Acid Methyl Ester I$_2$ (290 mg) was dissolved in 1.65 mL of a 0.23M solution of HCl in MeOH. It was mixed with 1-[4-(2-chloro-ethyl)-phenyl]-2-methyl-propan-1-one (200 mg) and with TMOF (400 mg). The mixture was heated at 100° C. for 10 minutes, cooled to room temperature and poured over 5 mL of a Na$_2$S$_2$O$_3$ solution. The mixture was extracted with DCM (2×5 mL). The organic layer was washed with a solution of Na$_2$S$_2$O$_3$ (5 mL), dried with anhydrous sodium sulfate and concentrated under vacuum. 0.220 g of 2-[4-(2-chloro-ethyl)-phenyl]-2-methyl-propionic acid methyl ester were obtained in a 96% yield and 70% purity. Alternatively, [4-(2-Chloro-ethyl)-phenyl]-2-methyl-propionic acid methyl ester was also obtained as in Example 4 but using ethyl chloroformate as the acid source instead of the solution of HCl in MeOH.

Productivity Comparison

In the following table, the productivity and process cycle times of the process of the invention is compared to those of the best or closest examples from the prior art. The productivity refers to the amount of product of formula (III) obtained based on the total amount of starting materials, reagents and solvents used in the process. This is a measure of the cost-efficiency of a process and so is of great importance for industrial scale production.

| Reference[a] | Examples | Productivity kg$_{output}$/kg$_{input}$[b] | Process cycle time[c] | Comment |
|---|---|---|---|---|
| WO2009/102155 | Ex. 1 and Ex. 5 | 0.062 | 20 h | Best results OMs product |
| WO2009/102155 | Ex. 1 and Ex. 7 | 0.017 | 20 h | Cl product |
| CN104151160A | Ex. 1 | 0.094[d] | 1 h | Best results OEt product (Not a leaving group) |
| Synth. Comm. 2011, 41, 1394. | Via Stille Coupling | 0.010 | 21 h | OMs product |
| CN104326909A | Ex. 1 and Ex. 4 | 0.063 | 24 h | Best results Br product |
| Invention | Ex. 1 and Ex. 2 | 0.106 | 2 h | Cl product |

[a]Patent CN 102675101 A does not contain a detailed experimental procedure.
[b]Measuring of the sum of the amounts of starting materials, reagents and solvents used in the reaction steps. Solvents and solutions used during the work up are not taken into account.
[c]Considering reaction times, without workup.
[d]Considering 1M concentration in toluene (typical commercial presentation) as there is no data of solvent volume.

As shown above, the process of the invention allows the preparation of compounds of formula (III) in a very high productivity and short reaction times. Consequently, this process is very cost-efficient and so very suitable for industrial production. Additionally, the process does not require the use or organometallic or highly toxic reagents, as in other prior art processes. Finally, the resulting compounds of formula (III) already include the leaving group required for subsequent reaction with the piperidinyl compound and so does not require additional reaction steps for its use in the preparation of Bilastine.

The invention claimed is:

1. A process for preparing a compound of formula (III)

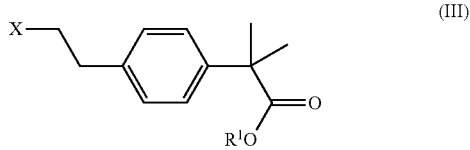

or a solvate thereof wherein
X is a leaving group; and
$R^1$ is $C_1$-$C_6$ alkyl;
which comprises oxidative rearrangement of a compound of formula (II) or a solvate thereof

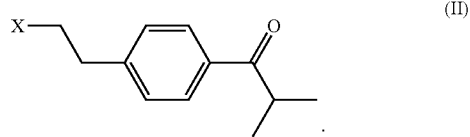

2. The process according to claim 1, which comprises:
(a) acylation of a compound of formula (I)

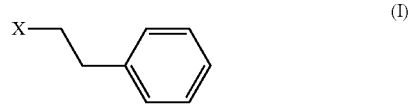

or a solvate thereof wherein X is a leaving group, to provide a compound of formula (II)

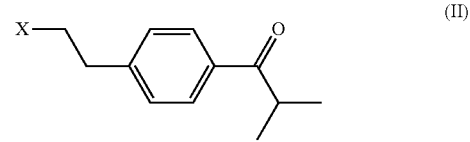

or a solvate thereof, and
(b) oxidative rearrangement of a compound of formula (II), or a solvate thereof, to provide a compound of formula (III)

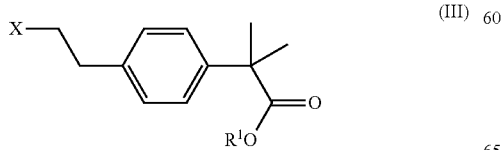

or a solvate thereof, wherein $R^1$ is $C_1$-$C_6$ alkyl.

3. The process according to claim 1, wherein X is selected from Cl, Br, I, OMs, OTs and OTf.

4. The process according to claim 1, wherein oxidative rearrangement is carried out in the presence of a tri($C_1$-$C_6$) alkyl orthoester, a ($C_1$-$C_6$)alkanol or a mixture thereof, an oxidizing agent and an acid catalyst.

5. The process according to claim 4, wherein the oxidizing agent is an iodine oxidizing agent.

6. The process according to claim 4, wherein the acid catalyst is selected from sulfuric acid, hydrochloric acid, hydrobromic acid, nitric acid, phosphoric acid, acetic acid, trifluoroacetic acid, camphorsulfonic acid, p-toluenesulfonic acid, methanesulfonic acid, maleic acid, fumaric acid, citric acid, oxalic acid, succinic acid, tartaric acid and malic acid.

7. The process according to claim 2, wherein acylation is carried out in the presence of an acylating agent selected from (iPrCO)$_2$O and a compound of formula iPrCO-Z, wherein Z is selected from OH, Cl, Br and I.

8. The process according to claims, wherein acylation is carried out in the presence of a protic acid and/or a Lewis acid.

9. The process according to claim 1, which comprises converting the compound of formula (III), or a solvate thereof, into Bilastine, or a salt or solvate thereof.

10. The process according to claim 2, which further comprises:
(c) reacting a compound of formula (III)

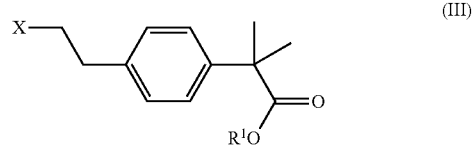

or a solvate thereof wherein
X is a leaving group; and
$R^1$ is $C_1$-$C_6$ alkyl;
with a compound of formula (IV)

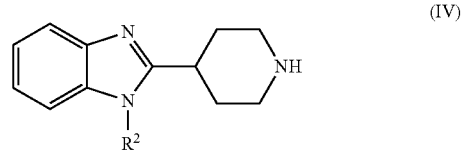

or a salt or solvate thereof wherein $R^2$ is selected from H and —CH$_2$CH$_2$OEt; to provide a compound of formula (V)

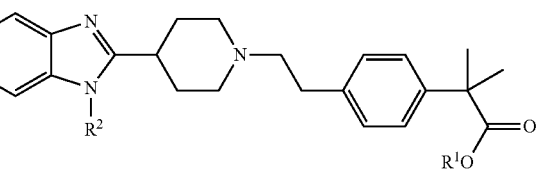

or a salt or solvate thereof; and
(d) converting the compound of formula (V), or a salt or solvate thereof, into Bilastine, or a salt or solvate thereof.

11. The process according to claim 10, wherein $R^2$ in the compounds of formula (IV) and (V) is —$CH_2CH_2OEt$ and step (d) comprises hydrolysis of the ester group in the compound of formula (V), or a salt or solvate thereof, to provide Bilastine, or a salt or solvate thereof.

12. The process according to claim 10, wherein $R^2$ in the compounds of formula (IV) and (V) is H and step (d) comprises:
   (d1) reacting a compound of formula (V), or a salt or solvate thereof, wherein $R^2$ is H, with a compound of formula (VI)

$$Y\diagup\diagdown OEt \quad (VI)$$

wherein Y is a leaving group,
   to provide a compound of formula (V), or a salt or solvate thereof, wherein $R^2$ is —$CH_2CH_2OEt$; and
   (d2) hydrolysis of the ester group in the compound of formula (V), or a salt or solvate thereof, wherein $R^2$ is —$CH_2CH_2OEt$ to provide Bilastine or a salt or solvate thereof.

13. The process according to claim 10, wherein step (d) comprises reacting a compound of formula (V), or a salt or solvate thereof, wherein $R^2$ is H with a compound of formula (VI)

$$Y\diagup\diagdown OEt \quad (VI)$$

wherein Y is a leaving group,
   and hydrolysis of the ester group in a compound of formula (V), or a salt or solvate thereof, to provide Bilastine or a salt or solvate thereof in a single reaction step.

14. The process according to claim 2, which further comprises:
   (c') hydrolysis of a compound of formula (III)

(III)

or a solvate thereof wherein
   X is a leaving group; and
   $R^1$ is $C_1$-$C_6$ alkyl;
   to provide a compound of formula (III')

(III')

or a salt or solvate thereof;
   (d') reacting a compound of formula (III'), or a salt or solvate thereof, with a compound of formula (IV)

(IV)

or a salt or solvate thereof wherein $R^2$ is selected from H and —$CH_2CH_2OEt$;
   to provide a compound of formula (V')

(V')

or a salt or solvate thereof; and
   (e') if needed, converting the compound of formula (V'), or a salt or solvate thereof, into Bilastine, or a salt or solvate thereof.

15. A compound of formula (II')

(II')

or a solvate thereof wherein X is selected from Cl, I, OMs, OTs and OTf.

16. The process according to claim 5, wherein the iodine oxidizing agent is selected from the group consisting of $I_2$, ICl, $ICl_3$, $HIO_3$, $PhI(OAc)_2$, $PhI(OCOCF_3)_2$, $PhI(OTf)_2$, $PhI(OH)OTs$, PhIO, NIS, IBX and DMP.

* * * * *

UNITED STATES PATENT AND TRADEMARK OFFICE
CERTIFICATE OF CORRECTION

PATENT NO. : 11,370,742 B2
APPLICATION NO. : 17/261731
DATED : June 28, 2022
INVENTOR(S) : Gonzalo Hernández Herrero et al.

Page 1 of 1

It is certified that error appears in the above-identified patent and that said Letters Patent is hereby corrected as shown below:

In the Claims

Claim 8, Column 20, Line 19 reads:
"The process according to claims, wherein acylation is"
Whereas it should read:
"The process according to claim 2, wherein acylation is"

Signed and Sealed this
Twenty-seventh Day of September, 2022

Katherine Kelly Vidal
*Director of the United States Patent and Trademark Office*